(12) United States Patent
Ehrman et al.

(10) Patent No.: US 12,280,132 B2
(45) Date of Patent: *Apr. 22, 2025

(54) SKIN CARE COMPOSITION

(71) Applicant: The Procter & Gamble Company, Cincinnati, OH (US)

(72) Inventors: Matthew Clair Ehrman, Singapore (SG); Wan Ting Chung, Singapore (SG); Zhi Yan Chew, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 18/070,575

(22) Filed: Nov. 29, 2022

(65) Prior Publication Data
US 2023/0165768 A1 Jun. 1, 2023

Related U.S. Application Data

(60) Provisional application No. 63/283,742, filed on Nov. 29, 2021.

(51) Int. Cl.
A61K 8/368 (2006.01)
A61K 8/34 (2006.01)
(Continued)

(52) U.S. Cl.
CPC ............. A61K 8/368 (2013.01); A61K 8/345 (2013.01); A61K 8/365 (2013.01); A61K 8/4926 (2013.01);
(Continued)

(58) Field of Classification Search
CPC ........ A61K 8/368; A61K 8/345; A61K 8/365; A61K 8/4926; A61K 2800/522; A61K 8/347; A61K 8/36; A61Q 19/08
(Continued)

(56) References Cited

U.S. PATENT DOCUMENTS 6,632,444 B1 10/2003 Zhou et al.
7,179,841 B2 2/2007 Zielinski et al.
(Continued)

FOREIGN PATENT DOCUMENTS

CN 106309156 A 1/2017
CN 110638692 A 1/2020
(Continued)

OTHER PUBLICATIONS

"Capryloyl Salicylic Acid: 78418-01-6." ChemicalBook, www.chemicalbook.com/ChemicalProductProperty_EN_CB2959760.htm# References. Accessed Oct. 12, 2023. (Year: 2023).*
(Continued)

Primary Examiner — Isaac Shomer
Assistant Examiner — Bryan James Rego
(74) Attorney, Agent, or Firm — Alexandra S. Anoff

(57) ABSTRACT

A low-pH, aqueous skin care composition, comprising: a) 0.1 to 10% of a hydroxycinnamic acid (HCA); and b) 0.1% to 5% of a hydrotrope selected from the group consisting of: phenolic acid, derivatives of phenolic acid, phenolic alcohol, derivatives of phenolic alcohol, and mixtures thereof; wherein the hydrotrope has a pKA less than the formula pH; and wherein the hydrotrope has the partition coefficient (logP) of less than 3.0; c) water, and wherein the pH of the composition is less than 5.0.

13 Claims, 2 Drawing Sheets

(51) Int. Cl.
  *A61K 8/365* (2006.01)
  *A61K 8/49* (2006.01)
  *A61Q 19/08* (2006.01)

(52) U.S. Cl.
  CPC ........ *A61Q 19/08* (2013.01); *A61K 2800/522* (2013.01)

(58) Field of Classification Search
  USPC .......................................................... 424/401
  See application file for complete search history.

(56) References Cited

U.S. PATENT DOCUMENTS

| | | | |
|---|---|---|---|
| 12,036,298 B2 * | 7/2024 | Ehrman | ................ A61K 8/675 |
| 12,144,882 B2 * | 11/2024 | Ehrman | ................ A61K 8/23 |
| 2005/0100517 A1 | 5/2005 | Sanzgiri et al. | |
| 2010/0189669 A1 | 7/2010 | Hakozaki | |
| 2014/0107046 A1 * | 4/2014 | Pan | ........................ A61K 8/498 514/456 |
| 2014/0161849 A1 | 6/2014 | Bickford | |
| 2014/0309294 A1 * | 10/2014 | Erfurt | ................... A23L 3/3517 426/321 |
| 2016/0101029 A1 | 4/2016 | Serrano Sanmiguel et al. | |
| 2016/0151270 A1 | 6/2016 | Brooks et al. | |
| 2018/0116936 A1 | 5/2018 | Pan et al. | |
| 2021/0346275 A1 * | 11/2021 | Carle | ................... A61Q 19/02 |
| 2023/0021127 A1 | 1/2023 | Maruyama | |
| 2023/0046148 A1 | 2/2023 | Stebbins et al. | |
| 2023/0165767 A1 | 6/2023 | Ehrman et al. | |

FOREIGN PATENT DOCUMENTS

| | | |
|---|---|---|
| CN | 112022766 A | 12/2020 |
| EP | 2906037 B1 | 8/2018 |
| WO | 0107004 A1 | 2/2001 |
| WO | 2005044214 A1 | 5/2005 |
| WO | 2008052674 A1 | 5/2008 |
| WO | 2011042073 A2 | 4/2011 |
| WO | 2013016257 A1 | 1/2013 |
| WO | 2019108450 A1 | 6/2019 |
| WO | 2020010036 A1 | 1/2020 |
| WO | 2020122088 A1 | 6/2020 |
| WO | WO-2021125070 A1 * | 6/2021 ............... A61K 8/11 |
| WO | 2021232040 A1 | 11/2021 |

OTHER PUBLICATIONS

Darwish, I A et al. "Effects of hydrotropic agents on the solubility, precipitation, and protein binding of etoposide." Journal of pharmaceutical sciences vol. 78,7 (1989): 577-81. doi:10.1002/jps.2600780714 (Year: 1989).*
Database GNPD [Online] Mintel; anonymous: "Acne Eliminating Gel", Jul. 31, 2020, 6 pages, XP093033428,Database accession No. 7945189.
Database GNPD [Online] Mintel; anonymous: "Advanced Brighten Treatment Serum", Aug. 17, 2020, 6 pages, XP093033429,Database accession No. 7974155.
Database GNPD [Online] Mintel; anonymous: "Haute C Bright Serum Concentrate", Jul. 6, 2020, 7 pages, XP093033427,Database accession No. 7935589.
Nair Nirmala et al, "26415 Regulation of postinflammatory hyperpigmentation by niacinamide through potential modulation of the protease inhibitor, SERPINB3", Journal of the American Academy of Dermatology, Mosby, Inc, US, vol. 85, No. 3, Aug. 7, 2021, 1 page, XP086725903, ISSN: 0190-9622.
PCT Search Report and Written Opinion for PCT/US2022/080526 dated May 26, 2023, 20 pages.
"Ferulic Acid and What it does for your skin", Online retrieved from "banish.com/blogs/ article/how-ferulic-acid-benefits-skin", 2021, 03 pages.
All Office Actions; U.S. Appl. No. 18/070,570, filed Nov. 29, 2022.
All Office Actions; U.S. Appl. No. 18/070,572, filed Nov. 29, 2022.
All Office Actions; U.S. Appl. No. 18/070,863, filed Nov. 29, 2022.
Unpublished U.S. Appl. No. 18/070,863, filed Nov. 29, 2022, to Matthew Clair Ehrman et al.
Unpublished U.S. Appl. No. 18/070,570, filed Nov. 29, 2022, to Matthew Clair Ehrman et al.
All Office Actions; U.S. Appl. No. 18/733,216, filed Jun. 4, 2024.
Unpublished U.S. Appl. No. 18/733,216, filed Jun. 4, 2024, Matthew Clair Ehrman et al.

* cited by examiner

SKIN CARE COMPOSITION

FIELD

The present disclosure generally relates to a low-pH, aqueous skin care composition, comprising: a) 0.1 to 10% of a hydroxycinnamic acid (HCA); and b) 0.1% to 5% of a hydrotrope selected from the group consisting of: phenolic acid, derivatives of phenolic acid, phenolic alcohol, derivatives of phenolic alcohol, and mixtures thereof; wherein the hydrotrope has a pKA less than the formula pH; and wherein the hydrotrope has the partition coefficient (logP) of less than 3.0; c) water, and wherein the pH of the composition is less than 5.0.

BACKGROUND

Skin is the first line of defense against environmental insults that would otherwise damage sensitive underlying tissue and organs. Additionally, skin plays a key role in a person's physical appearance. Not surprisingly, most people would like to have heathy, younger looking skin. Unfortunately for some people, the tell-tale signs of aging such as thinning skin, wrinkles, and age spots are an undesirable reminder of the disappearance of youth. The desire for healthy, younger looking skin has led to the development of numerous skin care products marketed to treat the various skin conditions associated with aging and unhealthy skin. These skin care products typically include one or more active ingredients for treating a skin condition of interest.

Antioxidants are commonly used in skin care products as active ingredients, for example, as disclosed in WO 2008/73684. And hydroxycinnamic acids (HCAs) are particularly well-known antioxidants, for example, as described in WO 2018/081790. However, the use of hydroxycinnamic acids in skin care composition can be problematic. For example, HCAs are relatively insoluble in water, which can lead to the undesirable formation of HCA crystals in the product. Further, when HCA is used at neutral pH (e.g., pH 5.0-8.0), which is common for skin care compositions, the HCA may oxidize or degrade, causing undesirable color changes, odors and/or reduced efficacy of the product. In some instances, formulating the composition at a lower pH may help stabilize the HCA, but it also lowers HCA solubility.

Hydroxycinnamic acids are relatively insoluble in water and aqueous compositions, and even less soluble at lower pH. In order to increase the solubility of the HCA, some formulators use additional solvents such as glycols, for example, as described in U.S. Pat. No. 9,072,919. However, this approach can have undesirable tradeoffs on the sensory profile of the composition. In particular, high levels of glycols may cause a skin care composition to feel undesirably oily because glycols generally do not dry or absorb into the skin quickly. Other attempts to address the solubility issues of hydroxycinnamic acid is to formulate the material into the oil phase of the composition (i.e., in the case of an emulsion) or to encapsulate the material. But these approaches can also be problematic. For example, adding a hydroxycinnamic acid to the oil phase can undesirably affect the sensory profile of the composition due to the introduction of oils and additional emulsifiers to the composition, and encapsulation can reduce the amount of hydroxycinnamic acid in the composition due to encapsulate loading limits. Thus, there remains a need to provide stabilized hydroxycinnamic acid in an aqueous composition at the desired level without undesirably affecting the sensory properties of the composition.

L'oreal WO2021125070A1 discloses a composition comprising: (a) at least one cinnamic acid derivative such as ferulic acid; (b) at least one lipophilic antioxidant; (c) at least one oil such as isopropyl lauroyl sarcosinate; and (d) water, wherein the pH of the composition is 4.5 or less.

L'oreal WO2021125070A1 also discloses in Examples, compositions comprising 0.5% ferulic acid, 6% of isopropyl lauroyl sarcosinate, 2% of dipropylene glycol, 10% of butylene glycol, and 3% of glycerin and 0.15% of Capryloyl salicylic acid.

There remains a need to improve HCA solubility and/or stability in low-pH compositions containing HCA.

SUMMARY

Disclosed herein is a low-pH, aqueous skin care composition, comprising: a) 0.1 to 10% of a hydroxycinnamic acid (HCA); and b) 0.1% to 5% of a hydrotrope selected from the group consisting of: phenolic acid, derivatives of phenolic acid, phenolic alcohol, derivatives of phenolic alcohol, and mixtures thereof; wherein the hydrotrope has a pKA less than the formula pH; and wherein the hydrotrope has the partition coefficient (logP) of less than 3.0; c) water, and wherein the pH of the composition is less than 5.0.

Also disclosed is a low-pH, aqueous skin care composition, wherein the HCA is a mixture of coumaric acid and ferulic acid, present at a ratio of 2:1 to 1:2.

BRIEF DESCRIPTION OF THE DRAWINGS

The HPLC reference spectrum for HCA and 4-VP are shown in FIGS. 1A and 1B, respectively.

DETAILED DESCRIPTION

Figure 1A:
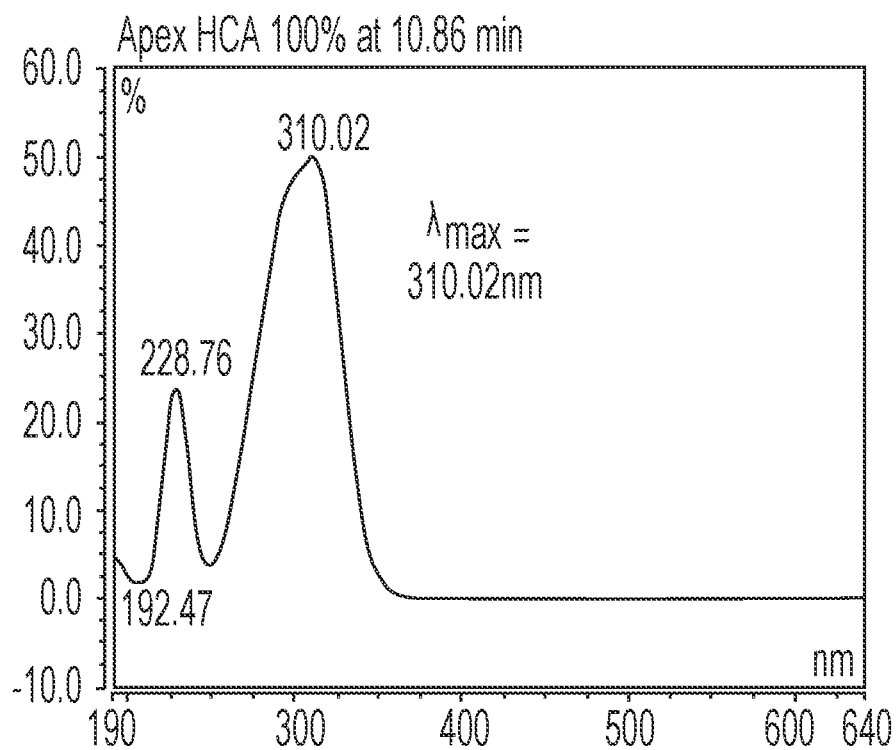
Figure 1B:
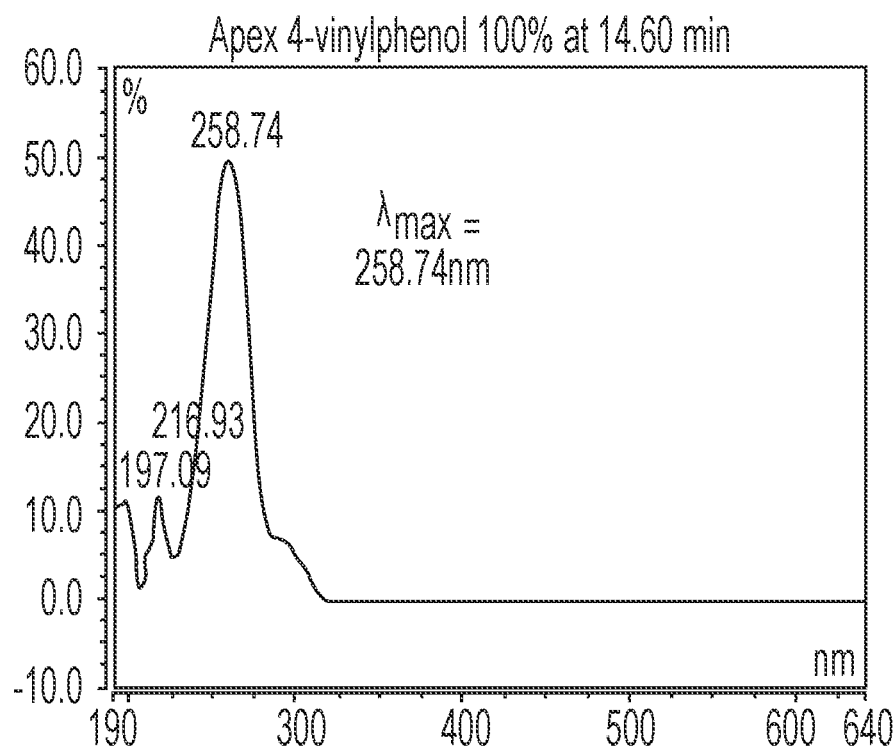
Figure 2:
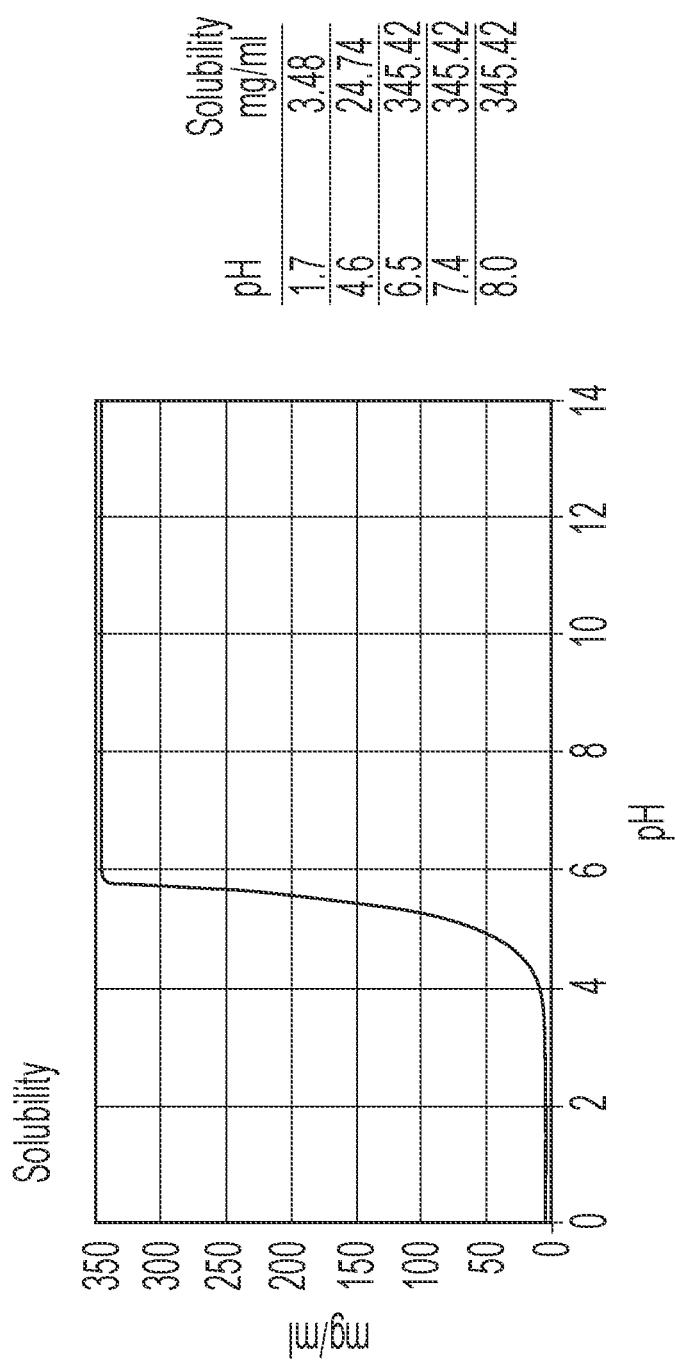
FIG. 2 illustrates HCA solubility in water across a range of pH. Chemicalize was used for prediction of HCA solubility (CAS #501-98-4, 7400-08-0), November 2021, chemicalize.com/, developed by ChemAxon®.

Hydroxycinnamic acids such as coumaric acid tend to exhibit undesirable solubility and/or stability characteristics in conventional skin care products. The insolubility of HCA is even worse in low-pH compositions. However, it was recently discovered that low-pH compositions can improve the efficacy of certain skin care actives such as niacinamide (see, U.S. Pat. No. 10,874,600). Thus, it would be particularly advantageous to improve HCA solubility and/or stability in such compositions.

Surprisingly, it has now been discovered that the stability and/or solubility characteristics of certain HCAs in a low-pH aqueous composition can be improved by formulating a low-pH aqueous composition with a suitable hydrotrope. In particular, certain HCA and hydrotrope combinations can act synergistically to combat the undesirable stability and/or solubility effects that other ingredients in the composition (e.g., niacinamide) have on the HCA. It has also been surprisingly discovered that a combination of ferulic acid and coumaric acid can synergistically improve the solubility of these materials in an aqueous, low-pH composition.

Reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

In all embodiments, all percentages are by weight of the cosmetic composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. All numeric ranges are inclusive of narrower ranges; delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods. As used in the description and the appended claims, the singular forms "a," "an," and "the" are intended to include the plural forms as well, unless the context clearly indicates otherwise.

Definitions

"About" modifies a particular value by referring to a range equal to plus or minus twenty percent (+/−20%) or less (e.g., less than 15%, 10%, or even less than 5%) of the stated value.

"Apply" or "application," as used in reference to a composition, means to apply or spread the compositions of the present invention onto a human skin surface such as the epidermis.

"Cosmetic agent" means any substance, as well any component thereof, intended to be rubbed, poured, sprinkled, sprayed, introduced into, or otherwise applied to a mammalian body or any part thereof to provide a cosmetic effect. Cosmetic agents may include substances that are Generally Recognized as Safe (GRAS) by the US Food and Drug Administration, food additives, and materials used in non-cosmetic consumer products including over-the-counter medications.

"Effective amount" means an amount of a compound or composition sufficient to significantly induce a positive benefit to keratinous tissue over the course of a treatment period. The positive benefit may be a health, appearance, and/or feel benefit, including, independently or in combination, the benefits disclosed herein. In a specific example, an effective amount of a vitamin B3 compound is an amount sufficient to improve the health and/or appearance of psoriatic skin during a treatment period. In some instances, an effective amount may be demonstrated using ex vivo and/or in vitro methods.

"Hydroxycinnamic acid" (HCA) refers to a class of aromatic acids or phenylpropanoids having a C6-C3 skeleton that are hydroxy derivatives of cinnamic acid. Some non-limiting examples of HCA are caffeic acid, cichoric acid, cinnamic acid, chlorogenic acid, diferulic acids, coumaric acids (p-, o-, and m-), ferulic acid, sinapinic acid, sinapic acid, and α-cyano-4-hydroxycinnamic acid.

"Improve the appearance of" means providing a measurable, desirable change or benefit in skin appearance, which may be quantified, for example, by a decrease in redness, inflammation, and/or plaque scales.

"Low-pH" means a pH of less than 5.0 (e.g., 1.5 to 4.9, 2.0 to 4.5, 2.5 to 4.0, or 3.5 to 4.0). A suitable method of determining the pH of a composition is described in more detail below.

"Neutral pH" means a pH of 5.0 to 8.0.

"Safe and effective amount" means an effective amount of an ingredient that is low enough to avoid serious side effects (within the scope of sound medical judgment).

"Skin care" means regulating and/or improving a skin condition. Some nonlimiting examples include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin exfoliation or desquamation, plumping the skin, improving skin barrier properties, improve skin tone, reducing the appearance of redness or skin blotches, and/or improving the brightness, radiancy, or translucency of skin.

"Skin care active" means a compound or combination of compounds that, when applied to skin, provide an acute and/or chronic benefit to skin or a type of cell commonly found therein. Skin care actives may regulate and/or improve skin or its associated cells (e.g., improve skin elasticity, hydration, skin barrier function, and/or cell metabolism).

"Skin care composition" means a composition that includes a skin care active and regulates and/or improves skin condition.

"Treatment period," as used herein, means the length of time and/or frequency that a material or composition is applied to a target skin surface.

Composition

The skin care compositions described herein are low-pH compositions intended for topical application to human skin to improve the appearance, health, and/or function of skin. The present compositions may be used for non-therapeutic (i.e., cosmetic) treatment of a variety of skin conditions. For example, the low-pH composition may be particularly suitable for improving the appearance of skin, especially fine lines, wrinkles, hyperpigmented spots, uneven skin tone, sallow looking skin and/or skin stability. Improved skin stability means to provide reduced day-to-day fluctuation of skin condition.

The low-pH skin care compositions herein include a safe and effective amount of hydroxycinnamic acid (e.g., p-coumaric acid, a.k.a. 4-HCA or p-HCA) and a suitable hydrotrope. The low-pH composition may also include a vitamin $B_3$ compound such as niacinamide and/or one or more other optional skin care actives. In some aspects, the composition may include a silicone emulsifier, a polymer thickener that can tolerate low-pH environments, a low molecular weight silicone fluid, an acid-salt pH-buffering system (e.g., a lactic acid/sodium lactate buffering system), and/or other ingredients commonly found in topical skin care compositions. It is believed, without being limited by theory, that the combinations of ingredients disclosed herein provides a stable and efficacious skin care composition that has good feel properties and is gentle on skin.

The low-pH compositions herein are formulated to provide improved HCA solubility in a low-pH environment. In an aqueous, low-pH skin care composition, HCA has a tendency to precipitate out of the composition and form crystals ("HCA crystals"), which can undesirably affect the look, feel, and/or efficacy of the composition. Conventional low-pH compositions often contain HCA crystals. However, the low-pH compositions herein contain a hydrotrope specifically selected to help solubilize the HCA and inhibit HCA crystallization, and thus are free of HCA crystals. A suitable method for determining whether a composition is free of HCA crystals and/or characterizing HCA crystals in a composition is described in more detail below.

The low-pH compositions herein are also formulated to provide improved HCA stability. HCAs are relatively good antioxidant materials, and thus tend to be oxidized and/or degrade over time, which can result in a skin care composition that exhibits an undesirable color change (e.g., yellowing), an undesirable odor, and/or reduced efficacy. Formulating at a lower pH can improve HCA stability by reducing the rate at which it is oxidized, but it may be desirable, in some aspects, to include an antioxidant in the low-pH composition to help further reduce oxidation and/or degradation of the HCA.

The low-pH skin care compositions herein can be made by mixing the ingredients with a dermatologically acceptable carrier using conventional methods known to those skilled in the art. The compositions may be provided in various product forms such as solutions, suspensions, lotions, creams, gels, toners, sticks, sprays, aerosols, ointments, cleansing liquid washes and solid bars, pastes, foams, mousses, shaving creams, wipes, strips, patches, electric-powered patches, hydrogels, film-forming products, facial and skin masks (with and without insoluble sheet), and the like. The composition form may follow from the particular dermatologically acceptable carrier chosen.

In some instances, the low-pH skin care composition herein may be in the form of an essence. An essence is a form of topical skin care composition in a relatively concentrated formula that typically has a lower viscosity than a conventional cream- or lotion-type skin care composition. An essence may be provided in the form of a low viscosity fluid that is marketed to specifically target a particular skin condition and/or be used in the first step of a skin care regimen. The skin care essence products herein can have a dynamic viscosity of 1 centipoise (cP) to 15,000 cP at 25° C. (e.g., 50 cP to 10,000 cP or 100 cP to 7,500 cP, 200 cp to 5,000 cp, or 300 cp to 2,500 cp). A method of determining the viscosity of the low-pH compositions is described in more detail in the Methods section below.

Hydroxycinnamic Acid

The low-pH skin care compositions herein include a safe and effective amount of HCA. The HCA may be present in the composition at 0.1% to 10% (e.g., 0.5% to 5% or 1% to 4%). Hydroxycinnamic acids are generally recognized as antioxidant phenolic compounds, which can be found in plants, mainly as a component of cell walls. See, H. K. Kuzaki et al., J. Agric. Food Chem., 50, 2161-68 (2002). In some aspects, it may be desirable to select coumaric acid for use in the low-pH composition, especially p-coumaric acid (a.k.a. 4-HCA). P-coumaric acid has the following structure:

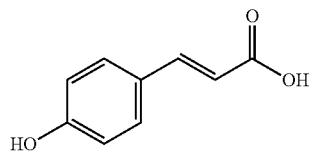 [SMILES: O=C(O)/C=C/c1ccc(O)cc1]

In other aspects, it may be desirable to use a mixture of two or more HCAs such as, for example, a mixture of coumaric acid and ferulic acid. In these aspects, the coumaric acid and ferulic acid may be present at a weight ratio of 2:1 to 1:2 (e.g., 1:1). A particularly suitable example of an HCA material suitable for use herein is LIPOBRITE available from Vantage™ Personal Care.

Hydrotrope

HCA compounds generally exhibit especially poor solubility in a low-pH aqueous composition, such as the low-pH compositions described herein. For example, p-coumaric acid has a solubility of approximately 345 mg/mL in water at pH 7.0 and 20° C. and a solubility of 4 mg/mL in water at pH 3.0 and 20° C. Without being limited by theory, it is believed that the decreased solubility of an HCA at lower pH is due to reduced ability of the HCA to undergo the acid dissociation that forms the conjugate base species observed at higher pH levels. At pH 7, p-coumaric acid exists at approximately 99.6% in its conjugate base form; whereas at pH 3, the conjugate base form is only present at approximately 13.4%. As a result of its relatively poor solubility, HCA tends to form crystals in an aqueous, low-pH skin care composition. HCA crystals can impart an undesirable feel to the composition during use (e.g., a rough or grainy feel) and/or may decrease the efficacy of the HCA and/or other ingredients in the composition. This can create an undesirable consumer perception of poor product quality. The compositions herein include 0.1% to 10% (e.g., 0.5% to 5% or 1% to 3%) of a hydrotrope to enhance the water solubility of HCA. It is preferred that the weight ratio between HCA and the hydrotrope is from about 2:1 to about 1:20, more preferably from about 1:1 to about 1:10, still more preferably from about 1:1 to about 1:5.

The hydrotropes useful herein have the partition coefficient (logP) of less than 3.0. The partition coefficient was calculated using the ACD Consensus algorithm calculations (perceptahelp.acdlabs.com/help_v2020/index.php/LogP #Consensus_LogP). Below are Some examples of ingredients and the partition coefficients are:

The hydrotrope should have a pKA less than the formula pH and a sufficient aqueous phase solubility at the formula pH to be fully soluble. Having an acidic pKa that is less than the pH of the composition can be especially important for low-pH compositions due to the reduced solubility of HCA at low pH. For example, sodium salicylate, which has a pKa of 2.8, may be a suitable hydrotrope for use in a composition with a pH of 3.8 because the carboxylic acid primarily exists in the conjugate base form. In contrast, cinnamic acid or sodium cinnamate, which have an acidic pKa of 4.32, would not be effective hydrotropes in this example. Furthermore, the hydrotrope should not form co-crystals with the target HCA. Additionally, the hydrotrope should be selected to help improve the sensory appeal of the composition by reducing the need for other solubilizing agents, such as glycols. Some non-limiting examples of hydrotropes that may be suitable for use herein are salicylic acid, 2, 4 dihydroxybenzoic acid, 2, 3 dihydroxybenzoic acid, 3-methoxy salicylic acid, salts of these, or a combination thereof. Other non-limiting examples of hydrotropes that may be suitable for use herein are disclosed in PCT Publication WO 2018/081790.

The hydrotropes useful herein have the partition coefficient (logP) of less than 3.0. The partition coefficient was calculated using the ACD Consensus algorithm calculations (http://perceptahelp.acdlabs.com/help_v2020/index.php/LogP#Consensus_LogP). Below are Some examples of ingredients and the partition coefficients are:

| CAS Number | SMILES | Name | logP[1] |
|---|---|---|---|
| 58-08-2 | Cnl cnc2c1c(=O)n(C)c(=O)n2C | Caffeine | 0.283 |
| 538-42-1 | [O-]C(=O)/C=C/c1ccccc.[Na+] | Sodium Cinnamate | 2.317 |
| 99-50-3 | C1=CC(=C(C=C1C(=O)O)O)O | 3,4-Dihydroxybenzoic Acid | 1.021 |
| 54-21-7 | OC(=O)c1ccccc1O.[Na] | Sodium salicylate | 2.371 |
| 89-86-1 | C1=CC(=C(C=C1O)O)C(=O)O | 2,4-Dihydroxybenzoic Acid | 1.744 |
| 877-22-5 | COC1=CC=CC(=C1O)C(=O)O | 3-Methoxysalicylic acid | 1.976 |
| 303-38-8 | C1=CC(=C(C(=C1)O)O)C(=O)O | 2,3-Dihydroxybenzoic acid | 1.534 |
| 70424-62-3 | CCCCCCCC(=O)OC1=CC=CC=C1C(=O)O | capryloyl salicylic acid | 4.599 |
| 7400-08-0 | c1cc(ccc1C=CC(=O)O)O | 4-hydroxycinnamic acid | 1.69 |

[1]logP ACD, Consensus algorithm

Vitamin $B_3$ compound

The present compositions include 0.1% to 10% (e.g., 0.5% to 5% or 1% to 4%) of a vitamin $B_3$ compound for regulating a variety of skin condition, for example, as described in U.S. Pat. No. 5,939,082. As used herein, "vitamin $B_3$ compound" means a compound having the formula:

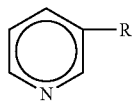

Where:
R is $CONH_2$ (i.e., niacinamide), COOH (i.e., nicotinic acid) or $CH_2OH$ (i.e., nicotinyl alcohol); derivatives thereof; and salts of any of the foregoing. Exemplary derivatives of vitamin $B_3$ compounds include nicotinic acid esters, including non-vasodilating esters of nicotinic acid (e.g., tocopheryl nicotinate, myristyl nicotinate) nicotinamide riboside, nicotinyl amino acids, nicotinyl alcohol esters of carboxylic acids, nicotinic acid N-oxide, and niacinamide N-oxide. In some instances, vitamin $B_3$ compounds such as niacinamide may have improved efficacy at lower pH, for example, as described in U.S. Publication No. 2020/0009123.

In some instances, it may be desirable for the ring nitrogen of the vitamin $B_3$ compound to be "uncomplexed" (e.g., chemically unbound and/or unhindered) in the composition and/or prior to application to a target skin surface. For example, the compositions herein may be free or substantially free (i.e., less than 3%, 2%, 1% or even less than 0.5%) of a salt or complex of a vitamin $B_3$ compound. Exemplary approaches to minimizing or preventing the formation of undesirable salts and/or complexes include omission of materials that form substantially irreversible or other undesirable complexes with the vitamin $B_3$ compound in the composition, pH adjustment, ionic strength adjustment, the use of surfactants, and practicing formulation processes wherein the vitamin $B_3$ compound and materials which complex therewith are in different phases.

Anti-Oxidant

The low-pH composition herein may include an antioxidant to combat HCA oxidation and/or degradation. The antioxidant, when included, may be present at 0.001% to 3% (e.g., 0.01% to 2%, 0.05% to 1%, or 0.1% to 0.5%). Some non-limiting examples of antioxidants that may be suitable for use herein are sodium sulfite, sodium bisulfite sodium metabisulfite, and butylated hydroxytoluene.

Low-pH Acid Buffering System

When providing a low-pH composition for topical application to skin, it can be important to include a buffering system to help maintain the pH of the composition for a period of time after it is applied to the skin (e.g., up to 5 minutes or more). On average, human skin pH typically ranges from about 5.0 to 6.0. To maintain this pH, human skin has evolved a natural buffering system that resists changes to pH. Thus, when a low-pH composition is applied to the skin, the skin's natural buffering system will try to adjust the pH of the composition to match the natural pH of the skin. Without the addition of the buffering agent, the low-pH composition may not be able to provide the desired skin care benefit. Accordingly, the compositions herein may include a low-pH acid buffering system.

The buffering agent may be selected according to the acid(s) that is used to lower the pH of the low-pH compositions herein. For example, lactic acid and gluconic acid may be used to lower the pH of the composition because they are generally considered to be gentler on skin (i.e., lower risk of irritation) compared to other alpha hydroxy acids. In this example, sodium lactate or sodium gluconate would then be selected to provide the acid/salt pH buffer system. The buffering agent may be present in the low-pH composition at 0.25% to 4% (e.g., 0.5% to 3%, 0.75% to 2% or 1% to 1.75%). A non-limiting example of a suitable low-pH buffer system for use herein is disclosed in co-pending U.S. Ser. No. 16/891,491. Of course, it is to be appreciated that the present composition may optionally include other pH buffers known for use in skin care compositions.

Thickeners

The composition includes a polymer thickener that can tolerate a low-pH, electrolytic environment. That is, the thickener will not lose its ability to thicken or stabilize the composition at low-pH in the presence of an acid-salt buffering system. Some conventional neutralized thickeners are known to degrade and/or lose the ability to suitably thicken a composition at lower pH and/or in the presence of an acid-salt buffer (e.g., sodium lactate). For example, some neutralized thickeners degrade in a low-pH environment. On the other hand, fatty alcohol thickeners such as cetyl alcohols and stearyl alcohols are generally stable at low-pH, but tend to impart an undesirable cloudiness or opacity to the composition when it is in the form of an essence, serum, or the like. It has also been found that certain anionic polymeric thickeners can provide suitable tolerance to low-pH environments but cannot tolerate buffer systems due to combination of acid and salt. Thus, in some instances, the low-pH composition described herein may be free or substantially free of neutralized thickeners, fatty alcohol thickeners, and anionic thickeners. The thickener may be present at 0.0001% to 25% (e.g., 0.001% to 20%, 0.01% to 10%, 0.5% to 7%, or 1% or 5%) by weight of the composition.

Other nonlimiting examples of thickeners or water structuring agents that may be used alone or in combination herein include natural or synthetic gums, polysaccharides, carboxylic acid polymers, polyacrylamide polymers, sulfonated polymers, and copolymers of these. Further examples include modified gums, celluloses, and superabsorbent polymers. The term "superabsorbent polymer" is understood to mean a polymer which is capable, in its dry state, of spontaneously absorbing at least 20 times its own weight of aqueous fluid, in particular of water and especially of distilled water. Suitable polysaccharides include alkyl hydroxyalkyl cellulose ethers, such as hydroxypropylmethylcellulose stearoxy ether. This material is sold under the tradename of SANGELOSE 60L and 90L from Daido Chemical Corp. Another suitable polysaccharide includes hydrophobically modified starch, such as Potato modified starch. This material is sold under the tradename of STRUCTURE SOLANACE by Nouryon®. Another polymer includes crosslinked polymers, the monomers of which are at least partially composed of acryloyldimethyltaurate monomers, such as, for example sodium polyacryloyldimethyl taurate, sold under the tradename of ARISTOFLEX SILK, from Clariant®.

It has now been found that certain anionic polymeric thickeners can provide suitable tolerance to low-pH environments and the desired feel and opacity properties to the composition. Thus, a particularly suitable example of an anionic thickener is polyacrylate crosspolymer-6, which is commercially available as SEPIMAX ZEN from Seppic®, France.

Low Molecular Weight Silicone Fluid.

In some instances, an anionic polymeric thickener may impart an undesirable tacky feel when the low-pH composition is applied to a target portion of skin. It has been found that the addition of a low molecular weight silicone fluid can reduce or prevent this tacky feel. The molecular weight of a silicone fluid depends on the length of its silicone polymer chain(s), which is also directly proportional to the viscosity of the silicone fluid. Thus, the low molecular weight silicone fluids suitable for use in the present low-pH composition have a kinematic viscosity of 100 cSt or less at 25° C. (e.g., 1 cSt to 90 cSt, 5 cSt to 50 cSt, or even 10 cSt to 30 cSt). Kinematic viscosity is a common method of classifying silicone fluids and can be obtained from the supplier of the material. A particularly suitable example of a low molecular weight silicone fluid is 5 cSt dimethicone fluid. As used herein, "dimethicone" means a polydimethyisiloxane compound having the formula:

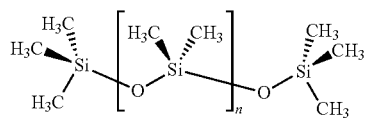

Dermatologically Acceptable Carrier

The low-pH compositions herein include a dermatologically acceptable carrier (which may be referred to as a "carrier"). The phrase "dermatologically acceptable carrier" means that the carrier is suitable for topical application to the keratinous tissue, has good aesthetic properties, is compatible with the actives in the composition, and will not cause any unreasonable safety or toxicity concerns. In one embodiment, the carrier is present at a level of from about 50% to about 99%, about 60% to about 98%, about 70% to about 98%, or, alternatively, from about 80% to about 95%, by weight of the composition.

The carrier can be in a wide variety of forms. In some instances, the solubility or dispersibility of the components (e.g., extracts, sunscreen active, additional components) may dictate the form and character of the carrier. Nonlimiting examples include simple solutions (e.g., aqueous or anhydrous), dispersions, emulsions, and solid forms (e.g., gels, sticks, flowable solids, or amorphous materials). In some instances, the dermatologically acceptable carrier is in the form of an emulsion. The emulsion may have a continuous aqueous phase (e.g., an oil-in-water or water-in-oil-in-water emulsion) or a continuous oil phase (e.g., water-in-oil or oil-in-water-in-oil emulsion). The oil phase of the present invention may comprise silicone oils, non-silicone oils such as hydrocarbon oils, esters, ethers, and mixtures thereof. The aqueous phase typically comprises water and water-soluble ingredients (e.g., water-soluble moisturizing agents, conditioning agents, anti-microbials, humectants and/or other skin care actives). However, in some instances, the aqueous phase may comprise components other than water, including but not limited to water-soluble moisturizing agents, conditioning agents, anti-microbials, humectants and/or other water-soluble skin care actives. In some instances, the non-water component of the composition comprises a humectant such as glycerin and/or other polyol(s).

In some instances, the compositions herein are in the form of an oil-in-water ("O/W") emulsion that provides a sensorial feel that is light and non-greasy. Suitable O/W emulsions herein may include a continuous aqueous phase of more than 50% by weight of the composition, and the remainder being the dispersed oil phase. The aqueous phase may include 1% to 99% water, based on the weight of the aqueous phase, along with any water soluble and/or water miscible ingredients. In these instances, the dispersed oil phase will typically be present at less than 30% by weight of composition (e.g., 1% to 20%, 2% to 15%, 3% to 12%, 4% to 10%, or even 5% to 8%) to help avoid some of the undesirable feel effects of oily compositions. The oil phase may include one or more volatile and/or non-volatile oils (e.g., botanical oils, silicone oils, and/or hydrocarbon oils). Some nonlimiting examples of oils that may be suitable for use in the present compositions are disclosed in U.S. Pat. No. 9,446,265 and U.S. Publication No. 2015/0196464.

The carrier may contain one or more dermatologically acceptable, hydrophilic diluents. As used herein, "diluent" includes materials in which the vitamin $B_3$ compound can be dispersed, dissolved, or otherwise incorporated. Hydrophilic diluents include water, organic hydrophilic diluents such as lower monovalent alcohols (e.g., $C_1$-$C_4$) and low molecular weight glycols and polyols, including propylene glycol, polyethylene glycol (e.g., molecular weight of 200 to 600 g/mole), polypropylene glycol (e.g., molecular weight of 425 to 2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof.

Emulsifier

When the low-pH composition herein is in the form of an emulsion (e.g., oil-in-water emulsion), it may be desirable to include an emulsifier to stabilize the emulsion (i.e., prevent the emulsion from phase separating). The emulsifier may be present in the composition at 0.01% to 10% (e.g., 0.05% to 5% or 0.1% to 2%). The emulsifiers may be nonionic, anionic or cationic. In some instances, the emulsifier may be a silicone emulsifier. Some non-limiting examples of emulsifiers that may be suitable for use herein are disclosed in U.S. Pat. Nos. 3,755,560; 4,421,769; and McCutcheon's Detergents and Emulsifiers, North American Edition, pages 317-324 (1986).

Some other non-limiting examples of emulsifiers that may be suitable for use herein include ethers of polyglycols and of fatty alcohols, esters of polyglycols and of fatty acids, ethers of polyglycols and of fatty alcohols which are glycosylated, esters of polyglycols and of fatty acids which are glycosylated, ethers of C12-30 alcohols and of glycerol or of polyglycerol, esters of C12-30 fatty acids and of glycerol or of polyglycerol, ethers of oxyalkylene-modified C12-30 alcohols and of glycerol or polyglycerol, ethers of C1-230 fatty alcohols comprising and of sucrose or of glucose, esters of sucrose and of C1230 fatty acids, esters of pentaerythritol and of C12-30 fatty acids, esters of sorbitol and/or of sorbitan and of C12 30 fatty acids, ethers of sorbitol and/or of sorbitan and of alkoxylated sorbitan, ethers of polyglycols and of cholesterol, esters of C12-30 fatty acids and of alkoxylated ethers of sorbitol and/or sorbitan, and combinations thereof. A particularly useful class of emulsifiers is polyethylene glycol ethers of lauryl alcohol such as laureth-1 through laureth-50 (e.g., laureth-4). Still other examples of emulsifiers include ethers of glycerol, polyglycerol, sucrose, glucose, or sorbitol; esters of glycerol, polyglycerol, sucrose, glucose, or sorbitol; and mixtures thereof. Other particularly useful classes of emulsifiers are the alkyl esters of sorbitol and sorbitol anhydrides such as polysorbate 20, polysorbate 21, and polysorbate 40.

In some aspects, it may be desirable to include a linear or branched silicone emulsifier in the low-pH composition. Particularly useful silicone emulsifiers include polyether modified silicones such as KF-6011, KF-6012, KF-6013, KF-6015, KF-6015, KF-6017, KF-6043, KF-6028, and KF-6038 and polyglycerolated linear or branched siloxane emulsifiers such as KF-6100, KF-6104, and KF-6105; all from Shin-Etsu. A particular suitable emulsifier for use herein is PEG-11 methyl ether dimethicone, which is available from Shin-Etsu as KF-6011. Surprisingly, it was discovered that the PEG-11 methyl ether dimethicone emulsifier further reduced the tacky feel of the anionic polymer thickener, thereby improving the overall feel of the low-pH composition. The emulsifier may be present at an amount of 0.1% to 10% (e.g., 1% to 5%, or 2%-4%).

Co-Solvent

In some aspects, the compositions herein may include a short chain dihydric alcohol (e.g., glycol) co-solvent to help solubilize the FICA. However, when glycol is selected as the co-solvent, it can be important to limit the amount of glycol to less than 25% (e.g., less than 20%, 17%, 15%, or even less than 10%) to reduce the risk of imparting undesirable feel characteristics to the composition having (e.g., sticky feeling or greasy feeling). Some non-limiting examples of glycols that may be suitable for use herein are propylene glycol, dipropylene glycol, butylene glycol, pentylene glycol, hexylene glycol, ethoxydiglycol, and C2-C6 polyethene glycols (e.g., PEG-3, PEG-4, PEG-4 methyl ether), and combinations thereof.

Other Optional Ingredients

The present composition may optionally include one or more additional ingredients commonly used in cosmetic compositions (e.g., colorants, skin care actives, anti-inflammatory agents, sunscreen agents, emulsifiers, buffers, rheology modifiers, combinations of these and the like), provided that the additional ingredients do not undesirably alter the skin health or appearance benefits provided by the present compositions. The additional ingredients, when incorporated into the composition, should be suitable for use in contact with human skin tissue without undue toxicity, incompatibility, instability, allergic response, and the like. Some nonlimiting examples of additional actives include vitamins, minerals, peptides and peptide derivatives, sugar amines, sunscreens, oil control agents, particulates, flavonoid compounds, hair growth regulators, antioxidants and/or anti-oxidant precursors, preservatives, protease inhibitors, tyrosinase inhibitors, anti-inflammatory agents, moisturizing agents, exfoliating agents, skin lightening agents, sunless tanning agents, lubricants, anti-acne actives, anti-cellulite actives, chelating agents, anti-wrinkle actives, anti-atrophy actives, phytosterols and/or plant hormones, N-acyl amino acid compounds, antimicrobials, and antifungals. Other non-limiting examples of additional ingredients and/or skin care actives that may be suitable for use herein are described in U.S. Publication Nos. 2002/0022040; 2003/0049212; 2004/0175347; 2006/0275237; 2007/0196344; 2008/0181956; 2008/0206373; 2010/00092408; 2008/0206373; 2010/0239510; 2010/0189669; 2010/0272667; 2011/0262025; 2011/0097286; US2012/0197016; 2012/0128683; 2012/0148515; 2012/0156146; and 2013/0022557; and U.S. Pat. Nos. 5,939,082; 5,872,112; 6,492,326; 6,696,049; 6,524,598; 5,972,359; and 6,174,533.

When including optional ingredients in the compositions herein, it may be desirable to select ingredients that do not form complexes or otherwise undesirably interact with other ingredients in the composition at low-pH, especially pH sensitive ingredients like niacinamide, salicylates and peptides. In some instances, it may be desirable to select skin care actives that function via different biological pathways so that the actives do not interfere with one another, which could reduce the efficacy of both agents. When present, the optional ingredients may be included at amounts of from 0.0001% to 50%; from 0.001% to 20%; or even from 0.01% to 10% (e.g., 50%, 40%, 30%, 20%, 10%, 5%, 4%, 3%, 2%, 1%, 0.5% or 0.1%), by weight of the composition.

Method of Use

The low-pH compositions herein are formulated for topical application to skin. The method of using the present low-pH composition involves identifying a target portion of skin on a person in need of treatment or where treatment is desired (e.g., portions of skin exhibiting uneven tone, sallowness, hyperpigmented spots, fine lines or wrinkles, skin stability) and applying an effective amount of the low-pH composition to the target portion of skin over the course of a treatment period. The effective amount of composition may vary based on the skin benefit desired by the user and/or the size of the treatment area. In some instances, the effective amount may range from 0.1 g to 5 g (e.g., 0.2 g to 4 g, 0.3 g to 2 g, or even 0.5 g to 1 g). The target portion of skin may be on a facial skin surface such as the forehead, perioral, chin, periorbital, nose, and/or cheek) or another part of the body (e.g., hands, arms, legs, back, chest). In some instances, a target portion of skin may be selected that does not currently exhibit signs of skin aging, but is an area of skin that commonly exhibits such features with age. In these instances, the low-pH composition may be used to help prevent the occurrence of such undesirable skin features.

The composition may be applied locally to the target portion of skin in need of treatment and, if desired, to the surrounding skin at least once a day, twice a day, or on a more frequent daily basis, during a treatment period. When applied twice daily, the first and second applications are separated by at least 1 to 12 hours. Typically, the composition is applied in the morning and/or in the evening before bed. When used according to the methods herein, the present compositions may improve the appearance and/or function of skin, for example, by improving skin texture. Improvements in skin texture can be provided, for example, by decreasing pore size, reducing skin roughness, reducing the presence and/or size of wrinkles, combinations of these and the like.

The treatment period is ideally of sufficient time for the low-pH composition to improve the appearance and/or function of the target portion of skin. The treatment period typically lasts for at least 1 week (e.g., about 2 weeks, 4 weeks, 8 weeks, or even 12 weeks). In some instances, the treatment period may extend over multiple months (i.e., 3-12 months). In some instances, the composition is applied most days of the week (e.g., at least 4, 5 or 6 days a week), at least once a day or even twice a day during a treatment period of at least 2 weeks, 4 weeks, 8 weeks, or 12 weeks.

The step of applying the composition herein may be accomplished by localized application. In reference to application of the composition, the terms "localized", "local", or "locally" mean that the composition is delivered to the targeted area (e.g., a psoriatic plaque) while minimizing delivery to skin surfaces where treatment is not desired. The composition may be applied and lightly massaged into an area of skin. The form of the composition or the dermatologically acceptable carrier should be selected to facilitate localized application. While certain embodiments herein contemplate applying a composition locally to an area, it will be appreciated that compositions herein can be applied more generally or broadly to one or more skin surfaces. In certain embodiments, the compositions herein may be used as part of a multi-step beauty regimen, wherein the present composition may be applied before and/or after one or more other compositions.

Methods

HPLC This method provides a way to determine the weight percentage of HCA and 4-vinylphenol (4-VP), respectively, in raw materials or finished products using high performance liquid chromatography ("HPLC"). This method may also be used to identify HCA and/or 4VP, by matching their wavelength spectrum and retention time to their respective known standards. The following instruments and materials are used in this method:

Instruments:
- a gradient HPLC system that includes a gradient HPLC pump, liquid auto-sampler, UV detector (and diode array detector (DAD) for spectrum analysis), and a suitable computing integrator or computer data system (e.g., a Waters 2695 HPLC system from Waters Corporation or equivalent).
- a 5 um, 250 mm×4.6 mm ID HPLC column (e.g., a C18 column from Alltech Alltima).

Method:
Two mobile phases are used to create the gradient with a consistent flow rate of 1.0 mL/min. Mobile phase A consists of 0.5% acetic acid in purified water. Mobile phase B consists of 0.5% acetic acid in acetonitrile. The gradient is illustrated below in Table 1.

TABLE 1

| Analysis Time | Mobile Phase Composition (v/v) | |
|---|---|---|
| | % A | % B |
| 0.00 | 90 | 10 |
| 6.00 | 90 | 10 |
| 7.00 | 50 | 50 |
| 12.00 | 50 | 50 |
| 13.00 | 30 | 70 |
| 16.00 | 30 | 70 |

Calculations:
1. Calculation of wt % of HCA in test samples $$HCA\ Wt\ \% = \frac{A \times M \times P \times 100}{B \times W}$$

A=Peak area ratio of HCA:Internal Standard in sample
B=Peak Area ratio of HCA:Internal Standard in Calibration Standard
M=Mass of HCA in mg, in Calibration Standard (~50 mg/50 mL×3 mL)
W=Sample weight in mg
P=Purity of HCA in decimal 2. Calculation of wt % of 4-VP in Finished Product Samples $$4VP\ Wt\% = \frac{a \times m \times p \times 100}{b \times w}$$

a=Peak area ratio of 4-VP: Internal Standard in sample
b=Peak area ratio of 4-VP: Internal Standard in Calibration Standard
m=Mass of 4-VP in mg, in Calibration Standard (~150 mg/100 mL×1 mL)
W=Sample weight in mg
p=Purity of 4-VP in decimal HCA Crystallization This method provides a way to determine HCA solubility in a composition by observing HCA crystals in situ. The method involves cycling the temperature of a test sample between freezing and thawing to imitate environmental conditions experienced by a skin care composition at an accelerated rate. This type of accelerated aging is commonly used in cosmetic product stability testing. HCA crystals can be detected using conventional means such as visual observation and microscopy.

A bulk sample of at least 10 g (e.g., 20 g-60 g) of the composition to be tested is placed in a suitable container that enables visual observation of the test sample (e.g., transparent plastic or glass jar). The test sample is subjected to 1 month of freeze/thaw temperature cycling to simulate environmental conditions that a skin care product may experience during shipping and storage. This is sometimes referred to as accelerated aging. The temperature cycling involves a 1-week freeze cycle at −7° C., followed by a 1-week thaw cycle at 25° C., and then repeating this freeze/cycle for a total temperature cycling time of 1 month.

Upon completion of the accelerated aging process (i.e., 1 month of temperature cycling), transparent test samples are visually inspected in-situ in the transparent container to determine if HCA crystallization/precipitation occurred. For opaque and translucent samples, the entire test sample is removed from the container and transferred to a suitable transparent substrate (e.g., plastic film or glass plate) and formed into a thin film of no more than 1 mm thickness. The sample is covered with a second transparent substrate to inhibit the loss of volatile ingredients during inspection. A light source (e.g., LED lamp or the like) is used to backlight the sample to aid in visual inspection. HCA crystals will generally appear as a precipitate in the composition visible to the naked eye when observed by someone with 20/20 vision from 45 cm away. Any precipitate identified during visual observation may be further evaluated using a microscope capable of providing fluorescent birefringence observation with cross-polarized light to identify anisotropic crystals. Any anisotropic crystal that has a longest dimension of greater than 0.1 mm is identified as an HCA crystal and the total number of HCA crystals is recorded. A test sample that contains no more than 1 HCA crystal is considered to be "free of HCA crystals" and is recorded as a "pass." A test sample that contains more than 1 HCA crystal, is recorded as a "fail."

While not required, fourier-transform infrared spectroscopy (FTIR) can be used to confirm that the HCA crystal or co-crystal contains the appropriate hydroxycinnamic acid structure. FTIR spectroscopy techniques are well-known in the art. See, U.S. Pat. No. 10,912,857, US2020/0000697, and Fourier Transform Infrared Spectroscopy in Colloid and Interface Science, D. R. Scheuing, Ed., American Chemical Society, 225, 1991.

Color

This method can be used to determine the change in color of a product, material, or target portion of skin. A spectrophotometer (e.g., Spectrophotometer CM-3600A, Konica Minolta, Japan, or equivalent) is used to measure spectrometric data for CIE (International Commission on Illumination) specified illuminating and viewing conditions, and compute the associated tristimulus values, XYZ, based on CIE observer and a CIE illuminant standards. The ASTM standard for obtaining spectrometric data for Object-Color Evaluation is ASTM E1164-12(2017)el with the values and procedures for computing CIE tristimulus values from spectrometric data outlined in ASTM E308. The CIELAB color scale, also referred to as L*a*b*, are calculated from the tristimulus values as defined in ASTM E308. The L* denotes the sample's perceptual lightness. Whereas a* and b* relate to the unique colors of human vision, with a* being positive in the red direction and negative in the green direction, and b* positive in the yellow direction and negative in the blue direction.

The spectrophotometer is operated with a 2° observer and D65 illuminant to measure 1931 CIE defined tristimulus XYZ values with and associated CIELAB colors. Portion samples are evaluated using a 10 mm path length in a plastic cell (e.g., CM-A131, Konica Minolta, Japan or equivalent), reflectance measurement, a 25.4 mm aperture opening at the specimen surface, and specular component excluded conditions with a standard white background. Acceptable white backgrounds include the white portion of an opacity card or equivalent (e.g., opacity card Form 2A, Leneta Company, Inc, Mahwah, N.J.). The instrument is calibrated with a zero standard, utilizing a zero-calibration box, or black trap, that is free from dust and debris (e.g., Konica Minolta zero calibration box CM-A155 or equivalent). The CIELAB values are reported by the associated instrument software (e.g., SpectroMagic NX) as defined in ASTM E308. For changes in product yellowness, the CIELAB color scale is utilized focused on the change in the b* value. The results are reported as a Δb*, where a positive Δb* indicates increased yellowness.

Rheology

This method provides a way to measure the dynamic viscosity of a composition or material using a BROOKFIELD brand viscometer (e.g., model DV2T or equivalent) and a suitable spindle (e.g., RV4 or equivalent) according to the manufacturer's instructions. It is to be appreciated that the skilled artisan will be able to select the appropriate spindle in accordance with the manufacturer's recommendation. After calibrating the viscometer, the spindle is immersed into a sufficient quantity of test sample (e.g., enough to immerse the spindle up to the immersion mark on the spindle shaft). Set the spindle rotation speed to 5 rpm, and then start the viscometer. Allow time for the indicated viscosity reading to stabilize (approximately 10-30 seconds). After the reading stabilizes, take 5 readings at 10 second intervals. Calculate the viscosity as the average of the 5 readings.

EXAMPLES

Example 1: Formulations

Table 2 below provides examples of low-pH skin care compositions that correspond to various aspects of the invention. The compositions can be prepared using conventional methods of making skin care compositions. Such methods typically involve mixing of the ingredients in one or more steps to a relatively uniform state, with or without heating, cooling, application of vacuum, and the like. All exemplified amounts exclude minor materials such as diluents, preservatives, color solutions, feel modifying powders and elastomers, etc., that may be present in a commercial product unless otherwise specified. HCA may be added as a solid form and solubilized in-situ, dissolved as a premix, or supplied as a predispersed raw material. A predispersed 15% solution of 4-HCA in PEG-4 (Lipobrite® from Vantage) is used for certain examples. For examples containing Lipobrite®, the 4-HCA and PEG-4 constituent levels are listed individually for clarity, with a superscript to denote the Lipobrite® raw material. The total Lipobrite® material added is the sum of the 4-HCA and PEG-4 constituents listed. All other materials are listed 'as is' from the suppliers and not broken down into the individual constituents.

Emulsions are prepared by first mixing the aqueous phase materials separately from the oil and/or silicone phase materials and then combining the two phases as appropriate to yield the desired continuous phase. In some aspects, the exemplary compositions can be made by blending the aqueous phase components with a suitable mixer (e.g., IKA RW20 or equivalent) until all materials are dissolved and homogeneous. When present, the optional polymer thickener may be hydrated by slowing adding the thickener directly into a water phase while stirring and continued mixing until homogeneous. The 4-HCA, hydrotrope, and optional glycol may be added together in a separate pre-mix container and mixed until fully dissolved and uniform. In some aspects, the hydrotrope may be pre-neutralized to form a suitable salt (e.g., sodium salicylate) to promote mixing/solubilization. The HCA premix can then be added to the main mix container and further mixed until homogeneous. The formula can be milled using a suitable mixer (e.g., IKA Ultra Turrax T-25 or equivalent) to reduce the emulsion particle size until a target viscosity is reached and uniform composition is achieved. The temperature may be adjusted as needed to control the speed of the process and/or achieve a homogenous final product.

TABLE 2

| Component | 2A | 2B | 2C % | 2D | 2E | 2F | 2G |
|---|---|---|---|---|---|---|---|
| Water | qs | qs | qs | qs | qs | qs | qs |
| Glycerin | 7.00 | 3.00 | 3.00 | 3.00 | 3.00 | 3.00 | 3.00 |
| Dimethicone 5 cSt | — | — | 2.00 | 2.00 | 2.00 | 2.00 | 2.00 |
| Niacinamide | 2.00 | 2.00 | 2.00 | 2.00 | 2.00 | 5.00 | 2.00 |
| Lactic acid | 1.80 | 1.80 | 1.80 | 1.80 | 1.80 | 1.80 | 1.80 |
| Sodium lactate | 1.30 | 1.30 | 1.30 | 1.30 | 1.30 | 1.30 | 1.30 |
| Polyacrylate crosspolymer-6 [1] | — | — | 1.25 | 1.25 | 1.25 | 1.25 | 1.25 |
| Sodium polyacryloyldimethyl taurate [2] | 1.25 | 1.25 | — | — | — | — | — |
| D-Panthenol | 0.50 | 0.50 | 0.50 | 0.50 | 0.50 | 0.50 | 0.50 |
| Disodium EDTA | 0.10 | 0.10 | 0.10 | 0.10 | 0.10 | 0.10 | 0.10 |
| PEG-11 methyl ether dimethicone [3] | — | — | 0.10 | 0.10 | 0.10 | 0.10 | 0.10 |
| Trehalose | — | — | 0.50 | 0.50 | 0.50 | 0.50 | 0.50 |
| Sodium benzoate | 0.05 | 0.05 | 0.05 | 0.05 | 0.05 | 0.05 | 0.05 |
| Sodium sulfite | — | 0.05 | 0.05 | 0.05 | 0.05 | 0.05 | 0.05 |
| 4-HCA [4] | 0.0001 | 1.00 | 0.50 | 0.25 | 0.10 | 1.00 | 0.30 |
| PEG-4 [4] | 0.00057 | 5.67 | 2.83 | 1.42 | 0.57 | 5.67 | 1.7 |
| Pentylene glycol | 0.10 | 3.00 | — | 3.00 | 3.00 | 3.00 | 3.00 |
| Propylene glycol | — | 5.00 | — | — | — | 5.00 | 5.00 |
| Dipropylene glycol | — | 4.00 | — | — | — | 4.00 | 4.00 |
| Ethoxydiglycol | — | 12.00 | 12.00 | 7.50 | 5.00 | 12.00 | 2.60 |
| Sodium Salicylate | — | 1.50 | 1.50 | 1.50 | 1.50 | 1.50 | 0.50 |
| Isohexadecane | 3.00 | 3.00 | — | — | — | — | — |
| Isopropyl Isostearate | 1.50 | 1.50 | — | — | — | — | — |
| Cetearyl glucoside and cetearyl | 0.50 | 0.50 | — | — | — | — | — |
| Behenyl Alcohol | 0.70 | 0.70 | — | — | — | — | — |
| Stearyl Alcohol | 1.20 | 1.20 | — | — | — | — | — |
| Cetyl Alcohol | 0.90 | 0.90 | — | — | — | — | — |
| PEG-100 Stearate | 0.10 | 0.10 | — | — | — | — | — |
| Stearic Acid | 0.10 | 0.10 | — | — | — | — | — |
| Dimethicone and Dimethiconol [5] | 1.00 | 1.00 | — | — | — | — | — |
| Palmitoyl pentapeptide-4 [6] | 0.50 | 0.50 | — | — | — | — | — |
| NaOH | * | * | * | * | * | * | * |
| HCl | * | * | * | * | * | * | * |
| pH | 4.0 | 4.0 | 4.0 | 4.0 | 3.0 | 5.0 | 3.8 |

| Component | 2H | 2I | 2J | 2K % | 2L | 2M | 2N |
|---|---|---|---|---|---|---|---|
| Water | qs | qs | qs | qs | qs | qs | qs |
| Glycerin | 3.00 | 3.00 | 3.00 | 7.00 | 3.00 | 3.00 | 3.00 |
| Dimethicone 5 cSt | 2.00 | 2.00 | — | — | 2.00 | 2.00 | 2.00 |
| Niacinamide | 2.00 | 2.00 | 2.00 | 0.25 | 0.50 | 0.50 | 2.00 |
| Lactic acid | 1.80 | 1.80 | 1.80 | 1.80 | 1.80 | 1.80 | 1.80 |
| Sodium lactate | 1.30 | 1.30 | 1.30 | 1.30 | 1.30 | 1.30 | 1.30 |
| Polyacrylate crosspolymer-6 [1] | 1.20 | 1.20 | 1.20 | 1.25 | 1.20 | 1.20 | 1.20 |
| Sodium polyacryloyldimethyl taurate [2] | — | — | — | — | — | — | — |
| Panthenol | 0.50 | 0.50 | 0.50 | 0.50 | 0.50 | 0.50 | 0.50 |
| Disodium EDTA | 0.10 | 0.10 | 0.10 | 0.10 | 0.10 | 0.10 | 0.10 |
| PEG-11 methyl ether dimethicone [3] | 0.10 | 0.10 | 0.10 | — | 0.10 | 0.10 | 0.10 |
| Trehalose | 0.10 | 0.10 | 0.10 | 0.10 | 0.10 | 0.10 | 0.10 |
| Sodium benzoate | 0.05 | 0.05 | 0.05 | 0.05 | 0.05 | 0.05 | 0.05 |
| Ferulic acid [7] | 0.25 | 0.25 | 0.25 | — | — | — | — |
| 4-HCA [4] | 0.25 | 0.25 | 0.25 | 0.10 | 0.5 | 0.5 | 0.5 |
| PEG-4 [4] | 1.42 | 1.42 | 1.42 | 0.57 | 2.83 | 2.83 | 2.83 |
| Pentylene glycol | 3 | — | — | — | — | — | — |
| Propylene glycol | — | — | — | — | — | — | — |
| Dipropylene glycol | — | — | — | — | — | — | — |
| Ethoxydiglycol | 15 | 15 | 15 | 5.00 | 15 | 20 | 15 |
| Sodium salicylate | — | 0.5 | 0.5 | 0.75 | 1.5 | 1.5 | 1.5 |
| Isohexadecane | — | — | 3.00 | 3.00 | — | — | — |
| Isopropyl isostearate | — | — | 1.50 | 1.50 | — | — | — |
| Cetearyl glucoside and cetearyl | — | — | 0.50 | 0.50 | — | — | — |
| Behenyl alcohol | — | — | 0.70 | 0.70 | — | — | — |
| Stearyl alcohol | — | — | 1.20 | 1.20 | — | — | — |
| Cetyl alcohol | — | — | 0.90 | 0.90 | — | — | — |

TABLE 2-continued

| | | | | | | | |
|---|---|---|---|---|---|---|---|
| PEG-100 stearate | — | — | 0.10 | 0.10 | — | — | — |
| Stearic acid | — | — | 0.10 | 0.10 | — | — | — |
| Dimethicone and dimethiconol [5] | — | — | 1.00 | 1.00 | 1.00 | — | — |
| Palmitoyl pentapeptide-4 [6] | — | — | 0.5 | 0.50 | — | — | — |
| NaOH | * | * | * | * | * | * | * |
| HCl | * | * | * | * | * | * | * |
| pH | 4.0 | 4.0 | 4.0 | 2.5 | 3.0 | 2.5 | 4.0 |

[1] SEPIMAX ZEN available from Seppic
[2] ARISTOFLEX SILK available from Clariant
[3] KF-6011 available from Shin-Etsu
[4] LIPOBRITE from Vantage (15% 4-HCA, 85% PEG-4)
[5] DC 1503 from Dow Corning
[6] PROMATRIXYL from Croda
[7] Ferulic Acid from Sigma Aldrich
* pH adjustment as necessary Example 2: Effect of pH and Niacinamide on HCA Stability This example demonstrates the effect of pH and niacinamide on HCA stability. When HCA degrades (e.g., via bacterial decarboxylation), it produces 4-vinylphenol as a byproduct, which is generally undesirable in a skin care composition. 4-VP can cause the composition to have an unpleasant odor and may further react to cause discoloration (e.g., yellowing) of the composition. Thus, it may be desirable to limit the amount of 4-VP in a skin care composition to less than 1500 ppm (e.g., less than 1100, 800 ppm, 700 ppm, 600 ppm, 500 ppm, 400 ppm, or even less than 300 ppm).

The compositions shown in Table 3 were tested to determine the effect of pH and niacinamide on the degradation of HCA and the formation of 4-VP. The pH of the test compositions was adjusted using a 6N HCL solution or 4% NaOH solution, as necessary. The test compositions were incubated at 50° C. for 3 weeks, and then tested according to the HPLC method described above for HCA degradation and the color method described above for changes in color (Ab*).

TABLE 3

| Component | 3A | 3B | 3C | 3D | 3E | 3F |
|---|---|---|---|---|---|---|
| | | | % | | | |
| Water | qs | qs | qs | qs | qs | qs |
| HCA | 1.0 | 1.0 | 1.0 | 1.0 | 1.0 | 1.0 |
| Niacinamide | 5 | 5 | 5 | 0 | 0 | 0 |
| Pentylene Glycol | 40 | 40 | 40 | 40 | 40 | 40 |
| pH | 3.56 | 4.57 | 6.17 | 3.45 | 4.52 | 6.10 |
| Results (3W50C) | | | | | | |
| HCA wt % (remaining) | 0.921 | 0.915 | 0.888 | 0.977 | 0.966 | 0.949 |
| 4-Vinylphenol | 380 | 700 | 1070 | 90 | 200 | 490 |
| Color Db* | 3.51 | 0.95 | 6.04 | 0.43 | 0.45 | 1.6 |

As can be seen in Table 3, both pH and niacinamide appear to affect HCA degradation, Δb* and 4-VP formation. These data suggest that increasing pH and/or adding niacinamide will increase the degradation of 4-HCA, increase the formation of 4-VP, and cause yellowing in an aqueous skin care composition. The data unexpectedly show that adding niacinamide actually accelerates the formation of 4-VP at higher pH. This is unexpected because it was previously unknown that niacinamide contributed to HCA degradation at all, let alone accelerated it. Thus, lowering the pH in a skin care composition comprising HCA and niacinamide appears to reduce the rate of formation of 4-VP more than expected.

The data in Table 3 also demonstrate that both pH and niacinamide contribute to the change in yellowness (Δb*) of the test compositions. Surprisingly, a pH of between 3.8 and 6.0 (e.g., about 4.5) appears to provide the lowest Δb* for the test compositions containing niacinamide. This result is surprising because it was believed that yellowing (i.e., a positive change in Ab* value) associated with HCA degradation would change with pH in a predictable linear fashion, as seen in with compositions 3D-3F.

Example 3: Effect of a Radical Scavenger on Rate of Yellowing

This example demonstrates the ability of an antioxidant to help reduce HCA degradation as evidenced by a reduced rate of yellowing (i.e., lower Ab* value). The test compositions shown in Table 4 below were tested with and without sodium metabisulfite, an oxygen-quenching, reducing agent, at pH 3.8 and pH 6.0. The test compositions were aged at two different accelerated aging conditions: 3 weeks at 50° C. (3W50C) and 3 months at 40° C. (3M40C). It is believed, without being limited by theory, that the accelerated aging conditions simulate environmental conditions that a skin care product may be exposed to during shipping and storage. Following the accelerated aging, the test compositions were tested according to the Color method described above to determine Ab*. The test composition aged for 3 months at 40° C. were further tested according to the HPLC method to determine the level of HCA degradation and 4-VP formation. The results of the testing are summarized in Table 4 below. As can be seen in Table 4, the addition of sodium metabisulfate (SMBS) significantly reduced the rate of yellowing for compositions 4B and 4D, as compared to 4A and 4C, respectively. Surprisingly, the data indicate that the effect of the oxygen quenching reducing agent was enhanced more than expected at low pH vs. neutral pH (i.e., 20% for 3WSOC and 240% for 3M40C, as can be seen in Table 5). The reduction in $\Delta b^*$ does not appear to be due to a further reduction of HCA degradation or 4-VP formation, but some other unique mechanism of action. Thus, it is now possible to provide combinations of ingredients that can synergistically reduce the rate of yellowing in a low-pH composition containing HCA.

TABLE 4

| Component | 4A | 4B % | 4C | 4D |
|---|---|---|---|---|
| Water | qs | qs | qs | qs |
| Glycerin | 4.5 | 4.5 | 4.5 | 4.5 |
| Dimethicone 5 eSt | 4.00 | 4.00 | 4.00 | 4.00 |
| Niacinamide | 2.00 | 2.00 | 2.00 | 2.00 |
| Lactic acid | 2.00 | 2.00 | — | — |
| Sodium lactate | 0.90 | 0.90 | — | — |
| Polyacrylate crosspolymer-6 | 1.50 | 1.50 | 1.50 | 1.50 |
| Panthenol | 0.50 | 0.50 | 0.50 | 0.50 |
| PEG-11 methyl ether dimethicone | 0.10 | 0.10 | 0.10 | 0.10 |
| Sodium Benzoate | 0.05 | 0.05 | 0.05 | 0.05 |
| 4-HCA | 1.00 | 1.00 | 1.00 | 1.00 |
| PEG-4 | 5.67 | 5.67 | 5.67 | 5.67 |
| Ethoxydiglycol | 20.0 | 20.0 | 20.0 | 20.0 |
| Sodium Metabisulfite | — | 0.05 | — | 0.05 |
| NaOH (adjust to target pH) | — | — | 0.22 | 0.22 |
| PH | 3.8 | 3.8 | 6 | 6 |
| Results (3W50C) | | | | |
| Db* value | 7.73 | 2.13 | 10.73 | 6.04 |
| Results (3M40C) | | | | |
| Db* value | 8.42 | 2.11 | 11.35 | 8.71 |
| HCA wt % remaining | 0.891 | 0.891 | 0.907 | 0.882 |
| 4-VP | 623 | 638 | 1044 | 980 |

The synergistic results from the testing in this example are illustrated in Table 5. Synergy factor is calculated by dividing the observed value by the expected value. A synergy factor of greater than 1 indicates a synergistic effect.

TABLE 5

Synergistic effect of radical scavenger

| | 3W50C Db* | 3M40C Db* |
|---|---|---|
| Control [4C] | 10.73 | 11.35 |
| pH Effect, pH 3.8 vs. pH 6 [4A-4C] | -3.00 | -2.93 |
| SMBS Effect at pH 6, [4D-4C] | -4.69 | -2.64 |
| 4B Expected [4D + (4A-4C)] AND/OR [4B+ (4D-4C)] | 3.04 | 5.78 |
| Expected combined effect [4B$_{expected}$ - 4C] | -7.69 | -5.57 |
| 4B Actual | 2.13 | 2.11 |
| Actual combined effect [4B actual - 4C] | -8.6 | -9.24 |
| Synergy Factor, [4B$_{actual}$ - 4C]/[4B$_{expected}$ - 4C] | 1.12 | 1.66 |

Example 5: Effect of Hydrotrope on HCA Solubility

The example demonstrates how a hydrotrope can improve the solubility of HCA. While it is desirable to formulate HCA containing compositions at lower pH to reduce 4-VP production and yellowing, the solubility of the HCA at low pH may not be sufficient for it to be added at levels needed for an effective skin care active. Similar to example 4, the test compositions shown in Table 6 were subjected to 2 freeze/thaw cycles at -7C/25C for 1 week/1 week, totaling one month of temperature cycling. As can be seen in Table 6, inventive combinations containing a suitable hydrotrope are free of HCA crystals ("pass"), while comparative examples demonstrate crystal formation ("fail").

The results of the testing are summarized in Tables 6 and 7 below. As can be seen in Table 6, the combination of ethoxydiglycol and sodium salicylate was able to solubilize 0.5% HCA in the low-pH aqueous composition, even when the level of glycol cosolvent is not sufficient alone. Further, as can be seen from the data, the addition of sodium salicylate reduces the amount of glycol to solubilize the HCA and, more importantly, remain below a level that might result in undesirable feel problem (e.g., <25%). Other well-known hydrotropes such as caffeine and niacinamide are unable to solubilize the HCA, even at higher levels (5%). Indeed, formulating at higher levels of niacinamide to boost HCA solubility can increase HCA degradation and yellowing, as demonstrated in Example 2 above. Additionally, it is also possible for a hydrotrope such as niacinamide to co-crystalize with HCA.

TABLE 6

| Material | 6A | 6B | 6C Wt % | 6D | 6E |
|---|---|---|---|---|---|
| Water | QS | QS | QS | QS | QS |
| Glycerin | 4.5 | 4.5 | 4.5 | 4.5 | 4.5 |
| Dimethicone, 5 cst | 4 | 4 | 4 | 4 | 4 |
| Niacinamide | 2 | 2 | 2 | 2 | 2 |
| Ethoxydigycol | 15 | 15 | 15 | 15 | 15 |
| 4-HCA | 0.5 | 0.5 | 0.5 | 0.5 | 0.5 |
| PEG-4 | 2.83 | 2.83 | 2.83 | 2.83 | 2.83 |
| Lactic acid | 1.8 | 1.8 | 1.8 | 1.8 | 1.8 |
| Sodium lactate | 1.3 | 1.3 | 1.3 | 1.3 | 1.3 |
| Polyacrylate crosspolymer-6 | 1.2 | 1.2 | 1.2 | 1.2 | 1.2 |
| PEG-11 methyl ether dimethicone | 0.1 | 0.1 | 0.1 | 0.1 | 0.1 |
| Caffeine | — | — | 5 | — | — |
| Sodium Cinnamate | — | — | — | 1.5 | — |
| Sodium Salicylate | 1.5 | — | — | — | — |
| 2,4-Dihydroxybenzoic Acid | — | — | — | — | 1.5 |
| 3,4-Dihydroxybenzoic Acid | — | — | — | — | — |
| 2,3-Dihydroxybenzoic acid | — | — | — | — | — |
| 3-Methoxysalicylic acid | — | — | — | — | — |
| Sodium hydroxide | * | * | * | * | * |
| Total | 100 | 100 | 100 | 100 | 100 |
| Target pH | 3.8 | 3.8 | 3.8 | 3.8 | 3.8 |
| Freeze/Thaw Crystallization | Pass | Fail | Fail | Fail | Pass |

| Material | 6F | 6G Wt % | 6H |
|---|---|---|---|
| Water | QS | QS | QS |
| Glycerin | 4.5 | 4.5 | 4.5 |
| Dimethicone, 5 cst | 4 | 4 | 4 |
| Niacinamide | 2 | 2 | 2 |
| Ethoxydigycol | 15 | 15 | 15 |
| 4-HCA | 0.5 | 0.5 | 0.5 |
| Lactic acid | 1.8 | 1.8 | 1.8 |
| Sodium lactate | 1.3 | 1.3 | 1.3 |
| Polyacrylate cross polymer-6 | 1.2 | 1.2 | 1.2 |
| PEG-11 methyl ether dimethicone | 0.1 | 0.1 | 0.1 |
| Caffeine | — | — | — |
| Sodium Cinnamate | — | — | — |

TABLE 6-continued

| | | | |
|---|---|---|---|
| Sodium Salicylate | — | — | — |
| 2,4-Dihydroxybenzoic Acid | — | — | — |
| 3,4-Dihydroxybenzoic Acid | 1.5 | — | — |
| 2,3-Dihydroxybenzoic acid | — | 1.5 | — |
| 3-Methoxysalicylic acid | — | — | 1.5 |
| Sodium hydroxide | * | * | * |
| Total | 100 | 100 | 100 |
| Target pH | 3.8 | 3.8 | 3.8 |
| Freeze/Thaw Crystallization | Fail | Pass | Pass |

*Sodium Hydroxide used as a pH adjuster as needed to target pH levels and neutralize phenolic acids As can be seen in Table 7, phenolic acids/alcohols with a pKA less than the formula pH, in this case 3.8, are more effective at solubilizing HCA than other traditional hydrotropes or chemicals of similar structural characteristics.

TABLE 7

| Hydrotrope | Level | pKA | Phenolic Alcohol or Phenolic Acid (Y/N) | pKA < pH | Crystallization |
|---|---|---|---|---|---|
| Caffeine | 5% | 14 | No | No | Fail |
| Sodium Cinnamate | 1.5% | 4.32 | Yes | No | Fail |
| 3,4-Dihydroxybenzoic Acid | 1.5% | 4.16 | Yes | No | Fail |
| Sodium salicylate | 1.5% | 2.79 | Yes | Yes | Pass |
| 2,4-Dihydroxybenzoic Acid | 1.5% | 3.10 | Yes | Yes | Pass |
| 3-Methoxysalicylic acid | 1.5% | 2.55 | Yes | Yes | Pass |
| 2,3-Dihydroxybenzoic acid | 1.5% | 2.56 | Yes | Yes | Pass |

Example 5: Solubility Effect of Mixing HCAs

This example demonstrates the unexpected improvement in solubility when a 50:50 mixture of p-coumaric acid and ferulic acid are included in an aqueous, low-pH composition, even in the absence of a hydrotrope. The test compositions shown in Table 8 were subjected to 2 freeze/thaw cycles at −7C/25C for 1 week/1 week, totaling one month of temperature cycling. As can be seen in Table 8, the test compositions did not exhibit significant HCA crystallization even in the absence of an additional hydrotrope. As can be seen in Table 8, the combination of ferulic acid and p-coumaric acid provided a synergistic boost in HCA solubility.

TABLE 8

| Material | 8A Wt % | 8B Wt % |
|---|---|---|
| Water | QS | QS |
| Glycerin | 4.5 | 4.5 |
| Dimethicone, 5 cst | 4 | 4 |
| Niacinamide | 2 | 2 |
| Ethoxydigycol | 15 | 15 |
| 4-HCA | 0.50 | 0.25 |
| Ferulic Acid | — | 0.25 |
| Lactic acid | 1.8 | 1.8 |
| Sodium lactate | 1.3 | 1.3 |
| Polyacrylate crosspolymer-6 | 1.2 | 1.2 |
| PEG-11 methyl ether dimethicone | 0.1 | 0.1 |
| Total | 100 | 100 |
| Target pH | 3.8 | 3.8 |
| Freeze/Thaw Crystallization | Fail | Pass |

Example 6: Comparative Examples

This example demonstrates the inability of conventional compositions to solubilize HCA at low pH. Example 2 of U.S. Publication number 2014/0107046 was prepared as described in the application, along with several variations of that formula (Examples A to K). The test compositions are shown below in Table 9. The test compositions were subjected to 2 freeze/thaw cycles at −7C/25C and 1 week/1 week, followed by a 90-day rest period at 25° C. After completion of the incubation period, the compositions were examined for the presence of HCA crystals, as described above. As can be seen in Table 9, all of the comparative compositions exhibited crystallization/precipitation. Even when p-coumaric acid is substituted for ferulic acid, as in comparative compositions C, I and J, the comparative compositions still exhibited HCA crystallization. Thus, none of the comparative compositions exhibit the desired HCA solubility provided by the inventive low-pH compositions herein.

TABLE 9

| Phase | Material | A | B | C | D | E | F | G |
|---|---|---|---|---|---|---|---|---|
| A | Propylene glycol | 10 | 10 | 10 | 10 | 10 | 10 | 10 |
| A | Dipropylene glycol | 10 | 10 | 10 | 10 | 10 | 10 | 10 |
| A | Ethanol | 10 | 10 | 10 | 10 | 10 | 10 | 10 |
| A | Ferulic acid | 0.5 | 0.5 | — | 0.5 | 0.5 | 0.5 | 0.5 |
| A | p-Coumaric acid | — | — | 0.5 | — | — | — | — |
| A | Baicalin | 0.4 | — | — | — | — | — | — |
| B | Water | 49 | 49.5 | 49.5 | 49.5 | 49.5 | 49.5 | 54.5 |
| B | Vitamin C | 10 | 10 | 10 | 10 | 10 | 10 | 10 |
| B | Caffeine | 5 | 5 | 5 | 5 | 5 | 5 | — |
| B | Nicotinamide | 5 | 5 | 5 | 5 | 5 | 5 | 5 |
| B | Baicalin | 0.1 | — | — | — | — | — | — |

TABLE 9-continued

| C | 10% NaOH (pH adjuster) | * | * | * | * | * | * | * |
|---|---|---|---|---|---|---|---|---|
| C | HCl (pH adjuster) | * | * | * | * | * | * | * |
| | Total | 100 | 100 | 100 | 100 | 100 | 100 | 100 |
| | Target pH | 4.5 | 4.5 | 4.5 | 4 | 3.5 | 3 | 3.8 |
| | Freeze/Thaw Crystallization? | Fail | Fail | Fail | Fail | Fail | Fail | Fail |

| Phase | Material | H | I | J | K |
|---|---|---|---|---|---|
| A | Propylene glycol | 10 | 10 | 10 | 10 |
| A | Dipropylene glycol | 10 | 10 | 10 | 10 |
| A | Ethanol | 10 | 10 | 10 | — |
| A | Ferulic acid | 0.5 | — | — | 0.5 |
| A | Baicalin | — | — | — | — |
| A | p-Coumaric acid | — | 0.5 | 0.5 | — |
| B | Water | 59.5 | 54.5 | 59.5 | 69.5 |
| B | Vitamin C | 10 | 10 | 10 | 10 |
| B | Caffeine | — | — | — | — |
| B | Nicotinamide | — | 5 | — | — |
| B | Baicalin | — | — | — | — |
| C | 10% NaOH (pH adjuster) | * | * | * | * |
| C | HCl (pH adjuster) | * | * | * | * |
| | Total | 100 | 100 | 100 | 100 |
| | Target pH | 3.8 | 3.8 | 3.8 | 3.8 |
| | Freeze/Thaw Crystallization? | Fail | Fail | Fail | Fail |

EXAMPLES/COMBINATIONS

1. A low-pH, aqueous skin care composition, comprising:
a) 0.1 to 10% of a hydroxycinnamic acid (HCA); and
b) 0.1% to 5% of a hydrotrope selected from the group consisting of: phenolic acid, derivatives of phenolic acid, phenolic alcohol, derivatives of phenolic alcohol, and mixtures thereof; wherein the hydrotrope has a pKA less than the formula pH; and wherein the hydrotrope has the partition coefficient (logP) of less than 3.0; and
c) water, wherein the pH of the composition is less than 5.0.

2. The composition of the preceding feature, wherein the weight ratio between HCA and the hydrotrope is from about 2:1 to about 1:20.

3. The composition of any of the preceding features, wherein the weight ratio between HCA and the hydrotrope is from about 1:1 to about 1:10.

4. The composition of any of the preceding features, wherein the weight ratio between HCA and the hydrotrope is from about 1:1 to about 1:5.

5. The composition of any of the preceding features, wherein the composition is free of HCA crystals.

6. The composition of any of the preceding features, further comprising from 0.1% to 10% of a vitamin $B_3$ compound.

7. The composition of any of the preceding features, wherein the vitamin $B_3$ compound is niacinamide.

8. The composition of any of the preceding features, wherein the hydrotrope is selected from the group consisting of hydrotrope selected from the group consisting of: phenolic acid, derivatives of phenolic acid, and mixtures thereof.

9. The composition of claim 8, wherein the hydrotrope is selected from sodium salicylate, 2,4 dihydroxybenzoic acid, 2,3 dihydroxybenzoic acid, 3-methoxy salicylic acid, salts of these, and combinations thereof.

10. The composition of any of the preceding features, further comprising less than 25% of a glycol co-solvent.

11. The composition of any of the preceding features, wherein the glycol co-solvent is selected from the group consisting of propylene glycol, dipropylene glycol, butylene glycol, pentylene glycol, hexylene glycol, ethoxydiglycol, C2-C6 polyethene glycols, and combinations thereof.

12. The composition of any of the preceding features, further comprising about 1% to about 20% by weight of an antioxidant.

13. The composition of any of the preceding features, wherein the antioxidant is selected from the group consisting of sodium sulfite, sodium bisulfite, and sodium metabisulfite, and combinations thereof.

14. The composition of any of the preceding features, wherein the pH is about 2.0 to about 4.5.

15. The composition of any of the preceding features, wherein the composition exhibits a $\Delta b^*$ of less than about 6 according to the Color method.

16. The composition of any of the preceding features, wherein the $\Delta b^*$ is less than about 2.5.

17. The composition of any of the preceding features, wherein the HCA is coumaric acid.

18. The composition of any of the preceding features, wherein the composition exhibits less than 25% HCA degradation according to the HPLC method.

19. The composition of any of the preceding features, further comprising less than 1000 ppm 4-vinylphenol.

20. A low-pH, aqueous skin care composition, comprising:
a) niacinamide;
b) a mixture of coumaric acid and ferulic acid, wherein the ratio of coumaric acid to ferulic acid is about 2:1 to about 1:2; and
c) water, wherein the composition has a pH of about 5.0 or less.

21. The composition of the preceding feature 20, wherein the weight ratio of coumaric acid to ferulic acid is 1:1.

22. The composition of the preceding feature 20, wherein the composition is free of HCA crystals.

23. The composition of the preceding feature 20, further comprising less than about 25% of a glycol co-solvent.

24. The composition of the preceding feature 20, further comprising a hydrotrope selected from sodium salicylate, 2,4 dihydroxybenzoic acid, 2,3 dihydroxybenzoic acid, 3-methoxy salicylic acid, salts of these, and combinations thereof.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A low-pH, aqueous skin care composition, comprising:
   a. 0.1% to 1% of a hydroxycinnamic acid (HCA), wherein the HCA comprises coumaric acid and ferulic acid; and
   b. 0.1% to 3% of a hydrotrope wherein the hydrotrope is selected from the group consisting of sodium salicylate, 2,4-dihydroxybenzoic acid, 3-methoxysalicylic acid, 2,3-dihydroxybenzoic acid, derivatives thereof, and mixtures thereof; and
   c. water;
   wherein the pH of the composition is from about 3.5 to about 4.5; and
   wherein the composition is free of HCA crystals and remains free of HCA crystals after 2 freeze/thaw cycles wherein a freeze/thaw cycle comprises freezing at −7° C. for a week followed by thawing at 25° C. for a week.

2. The composition of claim 1, wherein the weight ratio between HCA and the hydrotrope is from about 2:1 to about 1:20.

3. The composition of claim 2, wherein the weight ratio between HCA and the hydrotrope is from about 1:1 to about 1:5.

4. The composition of claim 1, further comprising from 0.1% to 10% of a vitamin B3 compound.

5. The composition of claim 1, further comprising less than 25% of a glycol co-solvent.

6. The composition of claim 5, wherein the glycol co-solvent is chosen from propylene glycol, dipropylene glycol, butylene glycol, pentylene glycol, hexylene glycol, ethoxydiglycol, C2-C6 polyethene glycols, or mixtures thereof.

7. The composition of claim 1, further comprising about 1% to about 20% by weight of an antioxidant.

8. The composition of claim 7, wherein the antioxidant is chosen from sodium sulfite, sodium bisulfite, and sodium metabisulfite, or mixtures thereof.

9. The composition of claim 1, wherein the composition exhibits a Δb* of less than about 6, according to the Color Method described herein.

10. The composition of claim 9, wherein the Δb* is less than about 2.5, according to the Color Method described herein.

11. The composition of claim 1, wherein the composition exhibits less than 25% HCA degradation according to the HPLC Method described herein.

12. The composition of claim 1, wherein the ratio of coumaric acid to ferulic acid is about 2:1 to about 1:2.

13. The composition of claim 12, wherein the weight ratio of coumaric acid to ferulic acid is about 1:1.

* * * * *